United States Patent [19]

Cirjak et al.

[11] Patent Number: 5,710,318
[45] Date of Patent: *Jan. 20, 1998

[54] FLUID BED PROCESS FOR THE ACETOXYLATION OF ETHYLENE IN THE PRODUCTION OF VINYL ACETATE

[75] Inventors: Larry M. Cirjak, Burton, Ohio; Michael F. Lemanski, Houston, Tex.; David R. Wagner, Lenexa, Kans.; Nancy C. Benkalowycz, Westlake, Ohio; Patricia R. Blum, Macedonia, Ohio; Marc A. Pepera, Northfield, Ohio; Christos Paparizos, Willowick, Ohio

[73] Assignee: The Standard Oil Company, Cleveland, Ohio

[*] Notice: The term of this patent shall not extend beyond the expiration date of Pat. No. 5,550,281.

[21] Appl. No.: 703,842

[22] Filed: Aug. 27, 1996

Related U.S. Application Data

[63] Continuation of Ser. No. 375,762, Jan. 20, 1995, abandoned, which is a continuation-in-part of Ser. No. 252,874, Jun. 2, 1994, Pat. No. 5,550,281.

[51] Int. Cl.⁶ .................................................. C07C 67/05
[52] U.S. Cl. ................................................. 560/245
[58] Field of Search .......................................... 560/245

[56] References Cited

U.S. PATENT DOCUMENTS

| | | |
|---|---|---|
| 2,800,506 | 7/1957 | Millidge et al. . |
| 2,825,740 | 3/1958 | Armstrong et al. . |
| 2,926,191 | 2/1960 | Lawson-Hall et al. . |
| 3,117,990 | 1/1964 | Adachi et al. . |
| 3,625,998 | 12/1971 | Fernholz ............ 560/245 |
| 3,670,014 | 6/1972 | Fernholz ............ 560/245 |
| 3,686,287 | 8/1972 | Knights . |
| 3,714,237 | 1/1973 | Calcagno ............ 560/245 |
| 3,743,607 | 7/1973 | Sennewald et al. . |
| 3,759,839 | 9/1973 | Fernholz et al. . |
| 3,761,513 | 9/1973 | Sennewald et al. . |
| 3,775,342 | 11/1973 | Kronig et al. . |
| 3,939,199 | 2/1976 | Fernholz ............ 560/245 |
| 3,948,983 | 4/1976 | Hackman et al. . |
| 3,950,400 | 4/1976 | Fernholz et al. . |
| 3,969,271 | 7/1976 | Lester . |
| 4,048,096 | 9/1977 | Bissot . |
| 4,087,622 | 5/1978 | Nakamura et al. . |
| 4,188,490 | 2/1980 | Hinsenkamp et al. . |
| 4,517,377 | 5/1985 | Isshiki et al. . |
| 4,933,204 | 6/1990 | Warren, Jr. et al. . |
| 4,978,778 | 12/1990 | Isshiki et al. . |
| 5,051,394 | 9/1991 | Haruta et al. . |
| 5,162,578 | 11/1992 | McCain et al. . |
| 5,179,056 | 1/1993 | Bartley . |
| 5,179,057 | 1/1993 | Bartley . |
| 5,185,308 | 2/1993 | Bartley et al. . |
| 5,314,858 | 5/1994 | Colling . |

FOREIGN PATENT DOCUMENTS

| | | |
|---|---|---|
| 0546677 | 6/1993 | European Pat. Off. . |
| 687990 | 12/1968 | South Africa . |
| 1266623 | 3/1972 | United Kingdom . |
| 1266624 | 3/1972 | United Kingdom . |
| 1283737 | 8/1972 | United Kingdom . |

OTHER PUBLICATIONS

Egloff, Reactions of Pure Hydrocarbons, (ACS Monograph Series #73) (1937) pp. 99–111 and 146.
Solomons, Organic Chemistry, 2nd ED., p. 266.
Chem Abstract 85:160560 (1976).
Derwent Abstract 93–025631/03 (1993).
T. Kawaguchi et al., Applied Catalysis, 36 (1988) 67–79.
T. Kawaguchi et al., *Applied Catalysis*, 32 (1987) 23–36.
T. Kawaguchi et al., J. Chem. Tech. Biotechnol., 42 (1988) 113–127.
Derwent abstract attached: Patent Abstracts of Japan, vol. 016 no. 033 (C–0905), 28 Jan. 1992, & JP-A-03 245844 (Japan Synthetic Rubber Co. LTD; Other: 01) 1 Nov. 1991, abstract.
Patent Abstracts of Japan, vol. 016 no. 098 (C–0918), 11 Mar. 1992, & JP-A-03 279349 (Tosoh Corp; Others: 01) 10 Dec. 1991, abstract.

*Primary Examiner*—Michael L. Shippen
*Attorney, Agent, or Firm*—Michael F. Esposito; David J. Untener

[57] ABSTRACT

A fluid bed process for the manufacture of vinyl acetate from ethylene, acetic acid and oxygen comprising feeding a gaseous mixture comprising ethylene and acetic acid into a fluid bed reactor through a first inlet, introducing the oxygen into the reactor through a second inlet, co-joining the oxygen, ethylene and acetic acid in the reactor in contact with a fluid bed catalyst to produce vinyl acetate. The particle size diameter of the particulate catalyst material has a range of 60% of the particles being below 200 microns (0.1 mm) with no more than 40% of the particles being below 40 microns (0.04 mm).

17 Claims, 1 Drawing Sheet

FLUID BED PROCESS FOR THE ACETOXYLATION OF ETHYLENE IN THE PRODUCTION OF VINYL ACETATE

This application is a continuation of U.S. Ser. No. 08/375,762 filed Jan. 20, 1995, now abandoned, which is a continuation-in-part of U.S. Ser. No. 08/252,874 filed Jun. 2, 1994, now U.S. Pat. No. 5,550,281.

BACKGROUND OF THE INVENTION

1. Field of the Invention

The present invention relates to a fluid bed process for oxyacylation of olefins or diolefins. In particular, the present invention is directed to a fluid bed process for the production of vinyl acetate from ethylene, acetic acid and an oxygen-containing gas in the presence of a fluid bed catalyst. More particular, the present invention is directed to a fluid bed process for the production of vinyl acetate using a palladium-gold-potassium fluid bed catalyst.

The commercial production of vinyl acetate by reacting ethylene, acetic acid and oxygen together in the gas phase in the presence of a fixed bed catalyst containing palladium, a promoter metal, and an alkali metal acetate is known. Usually the fixed bed catalyst components are supported on a porous carrier such as silica, zirconia or alumina. There are various patents such U.S. Pat. No. 3,759,839 and Great Britain Patent 1,266,623 which disclose the manufacture of vinyl acetate utilizing palladium-promoted catalyst. In each of these patents, mention is made of using a fluid bed process. However, in neither of these patents is there any mention of any technique or aspect of fluid bed procedures which would produce unexpected superior or economically beneficial results when compared to the fixed bed process. In fact, in each of these references, the typical conditions under which the process is run are fixed bed conditions.

There are numerous disadvantages related to the process of manufacture of vinyl acetate in a fixed bed procedure. Some of these disadvantages are:

1. The catalyst utilized continuously deactivates in the fixed bed reactor with time on-stream. This leads to a decline in vinyl acetate production. Thus, the product and recovery system must be designed to handle the high initial vinyl acetate yields and as the yields of vinyl acetate decline, a portion of the product recovery train is not utilized, thus, capital is wasted.

2. The fixed bed catalyst experiences uneven temperatures throughout the length of the reactor. Catalyst exposed to excessively high temperatures usually experiences premature aging. Catalyst residing in zones below the desired operating temperature will not optimally react to produce the maximum amount of vinyl acetate.

3. The per-pass conversion of ethylene is limited by the level of oxygen which is fed into the fixed bed reactor. In a fixed bed operation, the oxygen is premixed with the ethylene/diluent and acetic acid stream prior to entering the reactor. This complete feed mixture composition must be outside the flammability zone or the risk of explosion/fire results. Accordingly, the amount of oxygen which can be fed into the reactor is limited by the flammability limits of the mixture.

4. The vinyl acetate reaction in a fixed bed is seriously diffusion limited. Accordingly, much effort has gone into designing catalysts wherein the active components are located in a thin shell on the surface of the particles. Fixed bed catalysts which have a uniform dispersion of active material throughout the particle typically produce far fewer pounds of vinyl acetate per pound of noble metal than shell-type catalysts.

5. In a typical fixed bed procedure, catalyst activator (potassium acetate) must be continuously added as the reaction proceeds. This means that the activator is added at the inlet to the fixed bed reactor to replace the activator which exits the reactor. This method of addition of activator results in a non-uniform distribution of the activator upon the catalyst which, in turn, results in zones of less active and more active catalyst.

The fluid bed process of the present invention overcomes many of the disadvantages of the typical commercial fixed bed operation and achieves unexpected superior results compared to fixed bed processes. The advantages of the fluid bed process of the present invention will be more fully described below.

SUMMARY OF THE INVENTION

It is the primary object of the present invention to provide a fluid bed process for oxyacylation of olefins or diolefins.

It is a further object of the present invention to provide a fluid bed process for the manufacture of vinyl acetate from ethylene, acetic acid, and oxygen.

It is still another object of the present invention to provide a fluid bed process for the manufacture of vinyl acetate using a fluid bed palladium-based or palladium-gold-potassium base catalyst.

Additional objects and advantages of the invention will be set forth in part in the description which follows and in part will be obvious from the description or may be learned by practice of the invention. The objects and advantages of the invention may be realized and attained by means of the instrumentalities and combinations particularly pointed out in the appended claims.

To achieve the foregoing objects of the present invention, the process for manufacturing of vinyl acetate in a fluid bed reactor comprises feeding a gaseous mixture comprising ethylene and acetic acid into the fluid bed reactor through one or more inlets, feeding an oxygen-containing gas into the fluid bed reactor through at least one further inlet, co-joining the oxygen-containing gas, ethylene and acetic acid in the fluid bed reactor while in contact with a fluid bed catalyst material to enable the ethylene, acetic acid and oxygen to react to produce vinyl acetate and recovering the vinyl acetate from the fluid bed reactor.

In a preferred embodiment of the present invention the ethylene and acetic acid are fed into the reactor as a gaseous mixture through the one or more inlets.

In a further preferred embodiment of the present invention the ethylene and acetic acid gaseous mixture contains oxygen below its flammability limit in the mixture.

In another preferred embodiment of the present invention, the fluid bed catalyst utilized to practice the process of the present invention comprises a catalyst containing Pd, M, and A wherein M comprises Ba, Au, Cd, Bi, Cu, Mn, Fe, Co, Ce, U and mixtures thereof, and A comprises an alkali metal or mixtures thereof (preferably potassium). Typically, the weight percent of the palladium and alkali metal in the catalyst are 0.1 to 5.0 wt% palladium, preferably 0.5 to 2.0 wt%; alkali greater than 0 to 10 wt%, preferably 0.01 to 5 wt%. In addition, the weight percent of M may range from 0 to about 5 wt%, preferably greater than 0 to 5 wt%, especially preferred being 0.1 to 3 wt%. The fluid bed catalyst can be manufactured according to the procedures set forth in copending patent application Ser. No. 08/252,800, Atty Docket No. MFE-P-7114, assigned to the assignee of the instant application and herein incorporated by reference.

In a further preferred embodiment of the present invention the amount of catalyst including other fluidizable solids (e.g. inert particulates such as silica) present in the fluid bed reactor is maintained at a level sufficient to allow for the dissipation of the heat generated during the reaction so as to allow the reaction to proceed without damage to the catalyst.

In a still further preferred embodiment of the present invention, the fluid bed catalyst contains at least 60% of the catalyst particles at a diameter of below 200 microns (0.1 mm) and no more than 40% of the particles possessing a diameter being less than 40 microns (0.04 mm). Preferably, the catalyst particle diameter range is at least 50% of the particles being less than 100 microns (0.1 mm) and no more than 40% of the particles having a diameter being less than 40 microns (0.04 mm).

The operation of the fluid bed process of the present invention overcomes some of the distinct disadvantages described previously in the current commercial fixed bed operation to produce vinyl acetate. In the fluid bed process the catalyst is homogeneously continuously mixed in the reactor resulting in significant improvement in the homogeneous addition of the promoter even if it is introduced through a single outlet. Furthermore, the fluid bed operation allows for the continuous removal of a portion of deactivated catalyst and continuous replacement of catalyst during operation. This results in a steady state performance. In addition, a fluid bed reactor is nearly isothermal by design which minimizes catalyst deactivation due to exposure to excessive heat. Finally, in the fluid bed process of the present invention, typically, the oxygen is not mixed with the hydrocarbon until both are inside the reactor. Therefore, the catalyst is present when the feeds first mix at reaction temperature and the reaction proceeds immediately. This means that the oxygen partial pressure begins to drop at once. Alternatively, oxygen may be fed with a hydrogen-containing gas as in a typical fix bed operation while additional oxygen can be sparged into the reactor via the separate inlet. This unique feature of the fluid bed process allows significantly higher levels of oxygen to be safely employed in the conversion of acetic acid and ethylene to vinyl acetate without danger of flammability. The utilization of higher levels of oxygen permit substantially higher levels of ethylene and acetic acid conversion than are possible in the fixed bed processes.

DETAILED DESCRIPTION OF THE INVENTION

Figure 1:
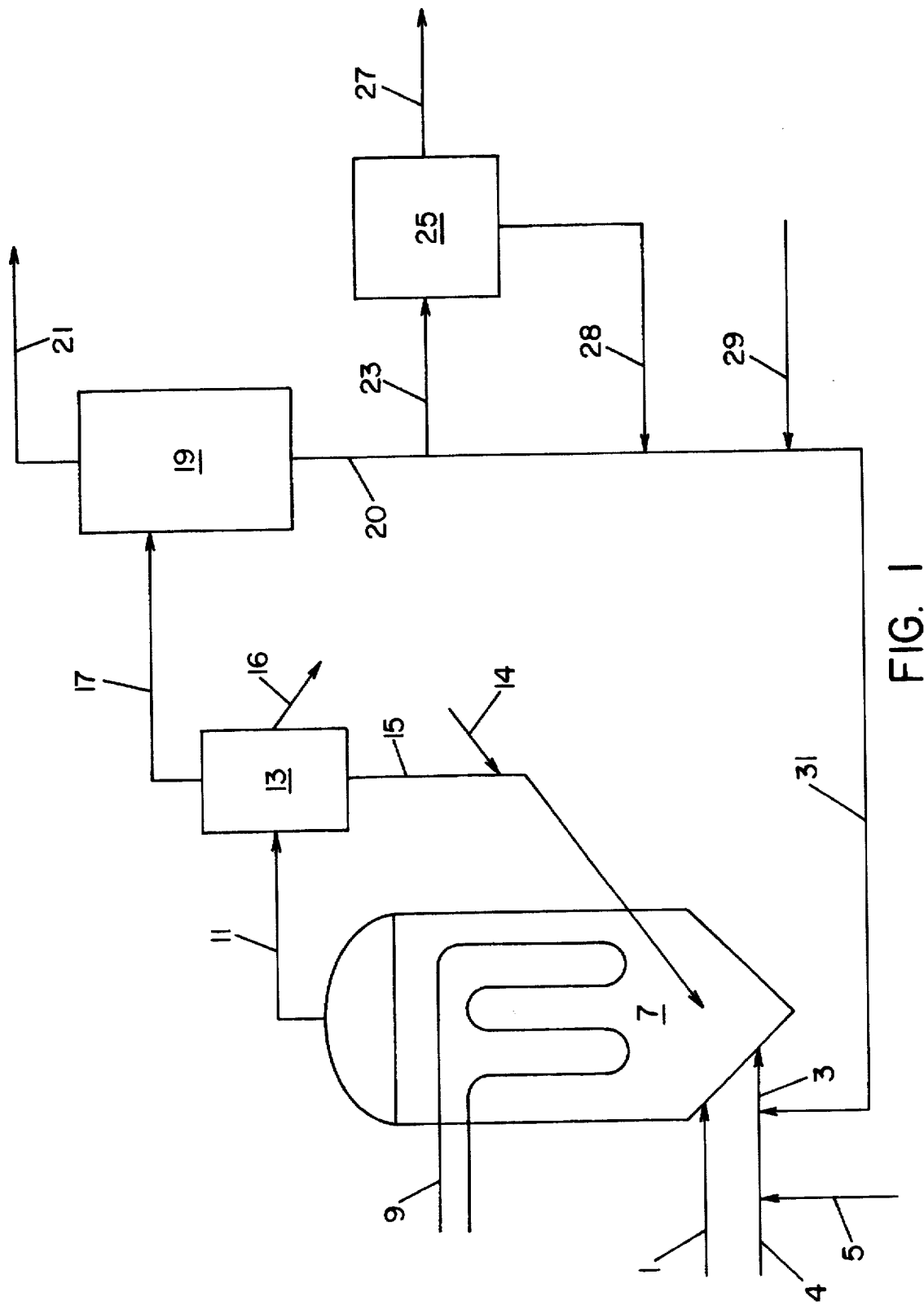
FIG. 1 is a schematic illustration of the process of the present invention.

In general, the process of the present invention comprises the manufacture of vinyl acetate in a fluid bed reactor comprising feeding a gaseous mixture comprising ethylene and acetic acid into a fluid bed reactor through a first inlet; feeding an oxygen-containing gas into the fluid bed reactor through a second inlet; co-joining the oxygen-containing gas, ethylene and acetic acid in the fluid bed reactor while in contact with a fluid bed catalyst to enable the ethylene, acetic acid and oxygen to react to produce vinyl acetate and recovering the vinyl acetate from the fluid bed reactor.

The general schematic for the fluid bed process of the present invention for the acetoxylation of ethylene to produce vinyl acetate (or the oxyacylation of olefins or diolefins in general) will now be set forth in detail with reference to FIG. 1.

Fluid bed reactor 7 containing a fluidizable microspheroidal catalyst is equipped with cooling coils 9 which provide for heat transfer from the reactor. Entering reactor 7 through line 3 is a mixture of ethylene and acetic acid. This mixture is dispersed within reactor 7 via a grid or sparger (not shown). It should be understood that the mixture of ethylene and acetic acid can be partially supplied by recycle of acetic acid and ethylene via line 31. In addition, oxygen may be added to the stream sent in via line 3 provided that the concentration of the oxygen in the stream is maintained below that which result in forming a flammable mixture.

Oxygen is fed into the reactor through line 1 as a separate stream and is dispersed in the reactor via a separate gas dispersion grid or sparger (not shown). The oxygen may be added in pure form or as an admixture with inert gas such as nitrogen or carbon dioxide. This stream of oxygen may also be mixed with low levels of hydrocarbons such as ethylene or acetic acid provided that, again, the mixture is still outside the flammability limits. Because the gas streams provided in lines 3 and 1 are never mixed prior to entry into the reactor and upon initiation of the reaction by the catalyst in the reactor, no flammable gas mixtures are produced.

The gaseous effluents produced in reactor 7 are passed through a cyclone and/or filter system 13 which separates any exiting solid catalyst from the gaseous product produced. The catalyst is then returned to the reactor via line 15 or collected for metals reclamation through line 16. In a preferred embodiment new catalyst may be supplied along with the recycled catalyst through line 14. Furthermore, promoter material may be added completely or partially to the catalyst system along with the new catalyst through line 14 thereby eliminating or supplementing the need to add promoter via line 5.

The gaseous reaction product stream exiting from the top of cyclone or filter 13 goes to product separation unit 19 via line 17 where a crude stream of vinyl acetate is recovered through line 21. Any recovery and purification procedure known in the art may be utilized, including those disclosed in U.S. Pat. No. 3,759,839 herein incorporated by reference or Great Britain Patent No. 1,266,623. The remaining stream containing unreacted ethylene, acetic acid, carbon dioxide (and/or other inerts), and oxygen is transported via line 20 for recycle to the fluid bed reactor. To prevent excessive accumulation of inerts including carbon dioxide in the recycle stream, a small slip stream may be transported via line 23 to an inert removal station 25 where inerts are removed and transported via line 27 for disposal while the remaining recycle stream is transported via line 28 back into line 31 for re-entry into reactor 7. Fresh ethylene may be supplied to the recycle stream 31 through line 29. Fresh acetic acid may be supplied through line 4 to the recycle stream for entry into reactor 7 via line 3.

The process is generally conducted at elevated pressures. Typically, pressures of 50 to 200 psig are used, preferably in the range of 75 to 150 psig. The reactor temperature can range typically from 100° to 250° C. with temperatures in the range of 135° to 190° C. being most preferred. In general, higher temperatures can more advantageously be employed with lower pressures.

Gaseous feed concentrations of ethylene, acetic acid and oxygen may vary. Typically useful ranges are as set forth below:

Ethylene—30 to 70%, preferably 35 to 65%, most preferably 40 to 60%:

Acetic Acid—10 to 25%, preferably 12 to 22%, most preferably 15 to 20%:

Oxygen—8 to 25%, preferably 9 to 15%.

The balance of the streams is composed of inert material such as carbon dioxide, nitrogen, argon and helium. The primary restriction on the feed composition is that the oxygen level in the effluent stream exiting the reactor be sufficiently low such that the gas stream exiting the fluid bed reactor is outside the flammability zone. This level is controlled by the amount of oxygen in the feed, the extent of oxygen conversion within the reactor and the concentration of inert in the effluent stream.

The following examples are set forth below only for purposes of illustration of the present invention.

EXAMPLES

Example 1: Preparation of Fixed Bed Catalyst as Reported in U.S. Pat. No. 5,185,308

A representative fixed bed catalyst of composition 0.91 wt% Pd, 0.34 wt% Au, and 3.2 wt% K on KA-160 silica spheres (5 mm) was prepared as follows.

The appropriate weights of $Na_2PdCl_4$ and $HAuCl_4$ were dissolved in 8.7 ml distilled water and impregnated on 15 g KA-160 silica spheres. The wet solid was allowed to sit undisturbed for several hours. An aqueous solution of sodium metasilicate was then poured onto the wet solid. Again the solid was left undisturbed overnight. An aqueous solution of hydrazine hydrate was then added to the solution covering the catalyst spheres. The wet solid was left undisturbed overnight. The solid was then drained and washed free of chloride with distilled water. The solid was dried at 60° C., the appropriate amount of potassium acetate in aqueous solution was then impregnated upon the solid and the finished catalyst was dried at 60° C.

Evaluation of this catalyst under the following conditions:

| Feed: | $C_2H_4$:HOAc:$O_2$:He = 53.1:10.4:7.7:28.6 |
| --- | --- |
| GHSV: | 3850/hr |
| Temp: | 150° C. (at hot spot) |
| Pressure: | 115 psig |
| Catalyst Charge: | 2.50 g |
| Catalyst Dilution: | 30 cc of 4 mm glass beads | produced 94.2% selectivity to vinyl acetate at 8.0% ethylene conversion (calculation based on the reported oxygen conversion of 32.2%).

Example 2: Preparation of Fluid Bed Catalyst

A catalyst with targeted composition corresponding to 0.90 wt% Pd, 0.40 wt% Au, 3.1 wt% K was prepared by the preferred method using the steps indicated above.

The $Na_2PdCl_4$ (8.57 g) and $HAuCl_4$ (2.18 g) were dissolved in 128 g of distilled water. This solution was then slowly added to 210 g of the spherical silica support (KA-160, Sud Chemie). The solution support mixture was swirled and gently shaken to insure even coverage. This mixture was allowed to sit for two hours at room temperature and essentially all the solution was absorbed into the support. A solution of 15.1 g of sodium metasilicate dissolved in 252 g of distilled water was poured onto the impregnated support. This mixture was allowed to sit for three hours. At this time 26.8 g of hydrazine hydrate was added and the mixture was permitted to sit overnight. The solid spheres were then washed thoroughly with distilled water to remove chloride from the solid. The solid was dried at 60° C. overnight, then the dried solid spheres were crushed. The crushed catalyst (200 g) was milled overnight with 133.3 g of silica sol (30 wt% $SiO_2$) and sufficient water to provide a millable consistency. The catalyst slurry was then spray dried to form microspheroidal particles. A portion of the microspheroidal solid (15 g) was then impregnated with 0.75 g of potassium acetate dissolved in 10 g of distilled water. This solid was dried at 60° C. overnight. Microscopic examination of the finished catalyst indicated well-formed microspheroidal particles.

Evaluation of the catalyst was carried out in a 40 cc fluid bed reactor under the conditions specified in Example 1 except the catalyst bed was composed of 7.5 grams catalyst diluted with sufficient inert silica fluid bed support to produce a total bed volume of 30 cc. An ethylene conversion of 5.2% with 93.7% selectivity to vinyl acetate was obtained, indicating that the preparation method employed was effective.

Examples 3–7: Effect of Process Variables on Fluid Bed Catalyst Performance

The catalyst prepared in Example 2 was tested in order to determine the effect of oxygen feed concentration, space velocity and temperature on performance. The percent ethylene fed was maintained constant and nitrogen fed was adjusted downward as oxygen or acetic acid levels increased. The following observations were noted:

TABLE I

| Example | 3 | 4 | 5 | 6 | 7 |
| --- | --- | --- | --- | --- | --- |
| % $O_2$ Fed | 7.7 | 15.4 | 15.4 | 15.4 | 15.4 |
| % $HOA_c$ Fed | 10.4 | 10.4 | 15.8 | 10.4 | 10.4 |
| T (deg-C.) | 160 | 160 | 160 | 160 | 170 |
| GHSV | 3080 | 3850 | 3850 | 3080 | 3080 |
| C2 = Conversion (%) | 6.0 | 7.4 | 7.7 | 8.5 | 10.2 |
| VAM Selectivity (%) | 93.0 | 90.6 | 92.5 | 91.2 | 86.4 |

Table I set forth above shows that good selectivity and conversion are maintained over a wide range of feed conditions.

Example 8: Preparation of Fluid Bed Catalyst

Dissolved 6.80 g of $Na_2PdCl_4$ and 1.73 g of $HAuCl_4$ in 110 g of distilled $H_2O$ and impregnated this solution on 200 g of KA-160 silica spheres (5 mm). Allowed wet solid to sit for two hours then added a solution of 12.0 g of $Na_2SiO_3$ in 240 g of distilled $H_2O$, mixed gently and allowed solid to sit undisturbed for 2 hours. To this mixture was added 21.3 g of 55% hydrazine hydrate. This mixture was allowed to sit overnight. Drained solution from solid and washed solid with fresh distilled $H_2O$ until negative test for chloride was obtained. The catalyst precursor spheres were then dried overnight at 60° C. 200 g of this catalyst precursor were crushed and mixed with 19.05 g crushed KA-160 (washed to remove Cl), 202.8 g of Snotex-N-30 silica sol (36 wt% solids), and sufficient water to provide a millable consistency to the slurry. This slurry was milled overnight, then spray dried. The microspheroidal catalyst particles were oven dried at 110° C. Elemental analysis of this solid found 0.62 wt% Pd and 0.23 wt% Au.

Dissolved 1.66 g of potassium acetate in 13.5 g of distilled $H_2O$ and impregnated this solution of 15.85 g of the above microspheroidal particles. After drying the solid contained 9.5 wt% potassium acetate.

Examples 9 through 12

A mixture of 14.5 g of the catalyst in Example 8 and sufficient fluidizable silica to provide 30 cc were placed in the fluid bed test reactor. The conditions and results are as follow:

| Example | 9 | 10 | 11 | 12 |
|---|---|---|---|---|
| % $C_2H_4$ fed | 50.2 | 48.4 | 45.6 | 45.9 |
| % $O_2$ fed | 5.3 | 8.6 | 9.7 | 8.9 |
| % HOAc fed | 10.3 | 9.9 | 13.5 | 13.7 |
| % $N_2$ fed | 34.3 | 33.1 | 31.2 | 31.4 |
| Total Flow | 380.8 | 394.3 | 418.5 | 415.9 |
| Temp (C.) | 156 | 157 | 165 | 158 |
| Pressure (psig) | 115 | 115 | 115 | 115 |
| $C_2H_4$ conversion (%) | 12.9 | 17.5 | 20.5 | 16.2 |
| VAM selectivity (%) | 90.0 | 87.7 | 86.1 | 89.3 |

Example 13

A 16.0 g portion of the catalyst prepared in Example 8 was calcined at 640° C. in air for 2 hours. To this calcined solid was added 1.6 g of potassium acetate dissolved in 13.5 g $H_2O$. The catalyst was then dried at 60° C.

Examples 14 and 15

16.05 g of the catalyst of Example 13 was mixed with sufficient inert microspheroidal silica to give 33 cc. This catalyst mixture was tested in a fluid bed reactor with the following results.

| Example | 14 | 15 |
|---|---|---|
| % $C_2H_4$ fed | 47.2 | 45.2 |
| % $O_2$ fed | 6.7 | 10.5 |
| % HOAc fed | 14.0 | 13.4 |
| % $N_2$ fed | 32.2 | 30.9 |
| Total Flow | 405 | 422.5 |
| Temp (C.) | 154 | 168 |
| Pressure (psig) | 115 | 115 |
| $C_2H_4$ conversion (%) | 11.1 | 16.9 |
| VAM selectivity (%) | 91.8 | 83.7 |

Example 16

A spray dried catalyst was prepared in the manner described in Example 8 except that it contained 17 wt% silica from the sol and levels of palladium and gold reagents were increased to give 0.69 wt% Pd and 0.25 wt% Au (no potassium acetate). 16 g of this microspheroidal solid was calcined 0.5 hours at 400° C. followed by 2 hours at 640° C. 1.57 g of potassium acetate dissolved in 13.5 g of distilled $H_2O$ was impregnated upon 15.0 g of the calcined solid. This final catalyst was dried at 60° C.

Examples 17 through 19

13.3 g of the catalyst of Example 16 was mixed with sufficient inert microspheroidal silica to give 30 cc. This catalyst mixture was tested in a fluid bed reactor with the following results.

| Example | 17 | 18 | 19 |
|---|---|---|---|
| % $C_2H_4$ fed | 47.9 | 45.6 | 44.8 |
| % $O_2$ fed | 5.1 | 9.7 | 11.1 |
| % HOAc fed | 14.2 | 13.6 | 13.4 |
| % $N_2$ fed | 32.7 | 31.0 | 30.6 |
| Total Flow | 399 | 419 | 426 |
| Temp (C.) | 151 | 158 | 167 |
| Pressure (psig) | 115 | 115 | 115 |
| $C_2H_4$ conversion (%) | 11.5 | 15.5 | 18.7 |
| VAM selectivity (%) | 92.0 | 89.3 | 86.0 |

While the invention has been described in conjunction with specific embodiments, it is evident that many alterations, modifications and variations will be apparent to those skilled in the art in light of the foregoing description. Accordingly, it is intended to embrace all such alternatives, modifications and variations as fall within the spirit and broad scope of the appended claims.

What we claim is:

1. The process for manufacturing vinyl acetate in a fluid bed reactor comprising co-joining an oxygen-containing gas, ethylene and acetic acid in a fluid bed reactor to react in the presence of a fluid bed catalyst material to produce vinyl acetate and recovering the vinyl acetate, wherein the improvement comprises feeding a gaseous mixture comprising ethylene and acetic acid into said fluid bed reactor through one or more inlets, feeding an oxygen-containing gas into said fluid bed reactor through at least one further inlet wherein the ratio of the sum of the ethylene, acetic acid and oxygen-containing gas entering the fluid bed reactor is within the flammability limits of a mixture of the gases.

2. The process of claim 1 wherein the ethylene and acetic acid gaseous mixture contains oxygen below its flammability limit in the mixture.

3. The process of claim 1 wherein the fluid bed catalyst comprises Pd, M, and A wherein M is selected from the group consisting of Ba, Au, Cd, Bi, Cu, Mn, Fe, Co, Ce, U and mixtures thereof and A is selected from the group consisting of an alkali metal and mixtures thereof.

4. The process of claim 3 comprising maintaining the amount of fluid bed catalyst material in said reactor at a volume sufficient to allow for the dissipation of heat generated during the reaction of the ethylene, acetic acid and oxygen-containing gas thereby enabling said reaction to proceed without damage to the fluid bed catalyst.

5. The process of claim 4 wherein said fluid bed catalyst material comprises a mixture of particulate catalytic material and particulate inert material.

6. The process of claim 5 wherein at least 60% of the particulate fluid bed catalytic material has a particle size diameter of below 200 microns and no more than 40% of the catalyst particles have a diameter less than 40 microns.

7. The process of claim 1 wherein the concentration of the ethylene in the combined gaseous feeds entering the reactor is between 30 to 70 volume percent.

8. The process of claim 7 wherein the concentration of the gaseous acetic acid in the combined gaseous feeds entering the reactor is between 10 to 25 volume percent.

9. The process of claim 8 wherein the concentration of the oxygen in the combined gaseous feeds entering the reactor is between 8 to 25 volume percent.

10. The process of claim 1 further comprising recycling at least a portion of the unreacted acetic acid, ethylene and oxygen into the fluid bed reactor.

11. The process of claim 10 further comprising recovering at least a portion of the fluid bed catalyst material escaping the fluid bed reactor and recycling said material into the fluid bed reactors.

12. The process of claim 1 wherein the pressure ranges from about 50 to 200 psig.

13. The process of claim 12 wherein the temperature ranges from between about 100° C. to 250° C.

14. The process of claim 1 further comprising recovering the fluid bed catalyst exiting the fluid bed reactor and recycling the recovered catalyst back into the reactor.

15. The process of claim 14 comprising adding a promoter for the fluid bed catalyst to the recycled fluid bed catalyst prior to recycle into the fluid bed reactor.

16. The process of claim 1 further comprising adding a promoter for the fluid bed catalyst to the fluid bed reactor.

17. The process of claim 1 wherein the promoter is added separately to the fluid bed reactor.

* * * * *